(12) United States Patent
Rabinovitz et al.

(10) Patent No.: US 11,331,474 B2
(45) Date of Patent: May 17, 2022

(54) LOW-PROFILE INTERCRANIAL DEVICE WITH ENHANCING GROUNDING TO ENSURE PROPER IMPEDANCE MEASUREMENTS

(71) Applicant: LONGEVITI NEURO SOLUTIONS LLC, Hunt Valley, MD (US)

(72) Inventors: Bradley Rabinovitz, Annapolis, MD (US); Corbin Clawson, Hampstead, MD (US); Jimmy Shah, Hunt Valley, MD (US)

(73) Assignee: LONGEVITI NEURO SOLUTIONS LLC, Hunt Valley, MD (US)

( * ) Notice: Subject to any disclaimer, the term of this patent is extended or adjusted under 35 U.S.C. 154(b) by 0 days.

(21) Appl. No.: 16/899,325

(22) Filed: Jun. 11, 2020

(65) Prior Publication Data

US 2020/0391022 A1    Dec. 17, 2020

Related U.S. Application Data

(60) Provisional application No. 62/860,396, filed on Jun. 12, 2019.

(51) Int. Cl.
*A61N 1/05* (2006.01)
*A61N 1/375* (2006.01)

(52) U.S. Cl.
CPC .................. *A61N 1/0539* (2013.01)

(58) Field of Classification Search
CPC .. A61N 1/0526; A61N 1/0529; A61N 1/0539; A61N 1/37514; A61N 1/0534; A61B 2576/026; A61B 5/6868; A61M 2210/0693; A61K 9/0085
See application file for complete search history.

(56) References Cited

U.S. PATENT DOCUMENTS

| | | | |
|---|---|---|---|
| 7,962,219 B2 | 6/2011 | Jaax et al. | |
| 8,454,701 B2 | 6/2013 | Devauchelle et al. | |
| 8,708,959 B2 | 4/2014 | Haase | |
| 9,409,022 B2 | 8/2016 | Jaax et al. | |
| 2005/0004620 A1* | 1/2005 | Singhal | A61N 1/3605 607/45 |
| 2008/0140149 A1* | 6/2008 | John | A61N 1/0531 607/45 |
| 2010/0160997 A1* | 6/2010 | Johnson | A61N 1/05 607/45 |
| 2014/0094674 A1 | 4/2014 | Nurmikko et al. | |
| 2018/0042726 A1* | 2/2018 | Yaremchuk | A61F 2/2875 |
| 2018/0091033 A1* | 3/2018 | Von Novak, III | H02K 44/16 |

\* cited by examiner

*Primary Examiner* — Carl H Layno
*Assistant Examiner* — Anh-Khoa N Dinh
(74) *Attorney, Agent, or Firm* — Welsh Flaxman & Gitler LLC

(57) ABSTRACT

A low-profile intercranial device adapted for housing a functional neurosurgical implant in manner providing for convenient and reliable grounding to ensure proper impedance measurements includes a static cranial implant including a base cranial implant member including an outer first surface, an inner second surface, and a recess shaped and dimensioned for receiving a functional neurosurgical implant. The low-profile intercranial device includes a plurality of fluid passageways extending between the inner second surface and the recess allowing for the flow of bodily fluid between an external environment of the base cranial implant member and a cavity defined by the recess.

36 Claims, 2 Drawing Sheets

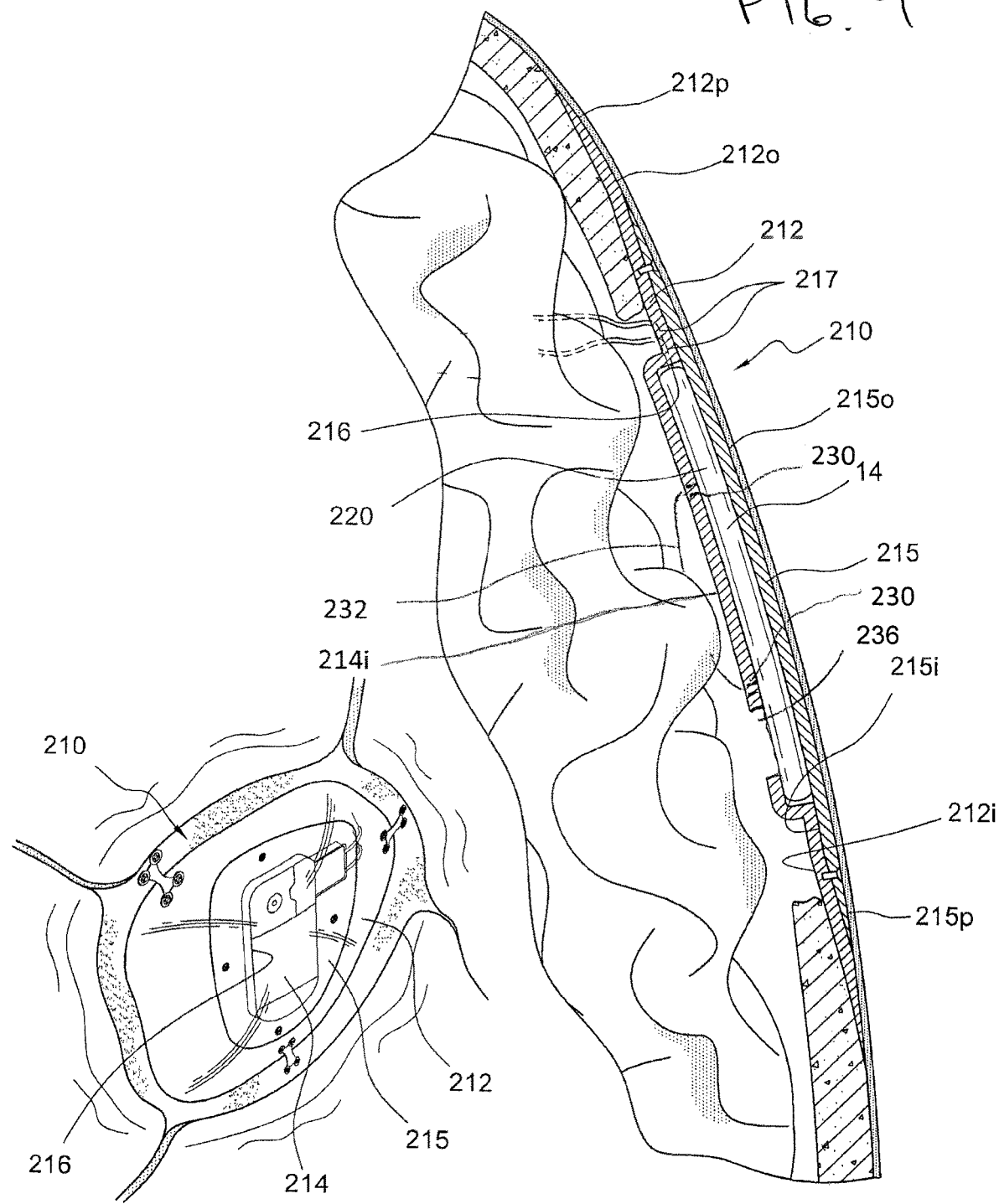

LOW-PROFILE INTERCRANIAL DEVICE WITH ENHANCING GROUNDING TO ENSURE PROPER IMPEDANCE MEASUREMENTS

CROSS REFERENCE TO RELATED APPLICATION

This application claims the benefit of U.S. Patent Application Ser. No. 62/860,396, entitled "LOW-PROFILE INTERCRANIAL DEVICE WITH ENHANCING GROUNDING TO ENSURE PROPER IMPEDANCE MEASUREMENTS," filed Jun. 12, 2019, which is incorporated herein by reference.

BACKGROUND OF THE INVENTION

1. Field of the Invention

The present invention relates to a static cranial implant enhancing the grounding of functional neurosurgical implant(s) housed within the static cranial implant.

2. Description of the Related Art

It is known that functional implants, such as stimulation devices, modulation devices, imaging devices, radiation therapy devices, remote sensing/monitoring devices etc., require grounding to operate properly. Depending upon the location of the implant, it may be difficult to achieve proper grounding and ultimately the proper functioning of the functional implant.

The present invention addresses this problem, especially the grounding of functional neurosurgical implants positioned within the skull in a patient.

SUMMARY

In one embodiment a low-profile intercranial device adapted for housing a functional neurosurgical implant in manner providing for convenient and reliable grounding to ensure proper impedance measurements includes a static cranial implant including a base cranial implant member including an outer first surface, an inner second surface, and a recess shaped and dimensioned for receiving a functional neurosurgical implant. The low-profile intercranial device includes at least one fluid passageway providing for convenient and reliable grounding of a functional neurosurgical implant. The at least one fluid passageway extending between the inner second surface and the recess allowing for the flow of bodily fluid between an external environment of the base cranial implant member and a cavity defined by the recess.

In some embodiments the static cranial implant further includes a cover cranial implant member.

In some embodiments the base cranial implant member has a geometry that substantially conforms with a resected portion of the patient's anatomy.

In some embodiments the center recess includes internal side walls and a recess base surface, and the at least one fluid passageway extends between the inner second surface and the recess base surface.

In some embodiments a functional neurosurgical implant is positioned within the recess.

In some embodiments the at least one fluid passageway is a crescent shaped aperture.

In some embodiments the at least one fluid passageway includes a plurality of fluid passageways.

In some embodiments the plurality of fluid passageways are formed in opposed corners of the recess.

In some embodiments suture holes a provided within a recess base surface of the recess.

In some embodiments the base cranial implant member is made of a clear material.

In some embodiments the at least one fluid passageway is shaped and dimensioned to allow for fluid communication syphoning heat from the intercranial device.

In some embodiments the at least one fluid passageway is shaped and dimensioned to allow for fluid communication syphoning cold from the intercranial device.

In some embodiments the at least one fluid passageway is shaped and dimensioned to prevent fluid accumulation within the intercranial device.

Other advantages of the present invention will become apparent from the following detailed description when viewed in conjunction with the accompanying drawings, which set forth certain embodiments of the invention.

BRIEF DESCRIPTION OF THE DRAWINGS

FIG. 3 is an installed perspective view of the low-profile intercranial device shown in FIGS. 1 and 2.

FIG. 4 is a sectional view of the fully installed low-profile intercranial device shown in FIG. 3.

DESCRIPTION OF THE PREFERRED EMBODIMENTS

Figure 1:
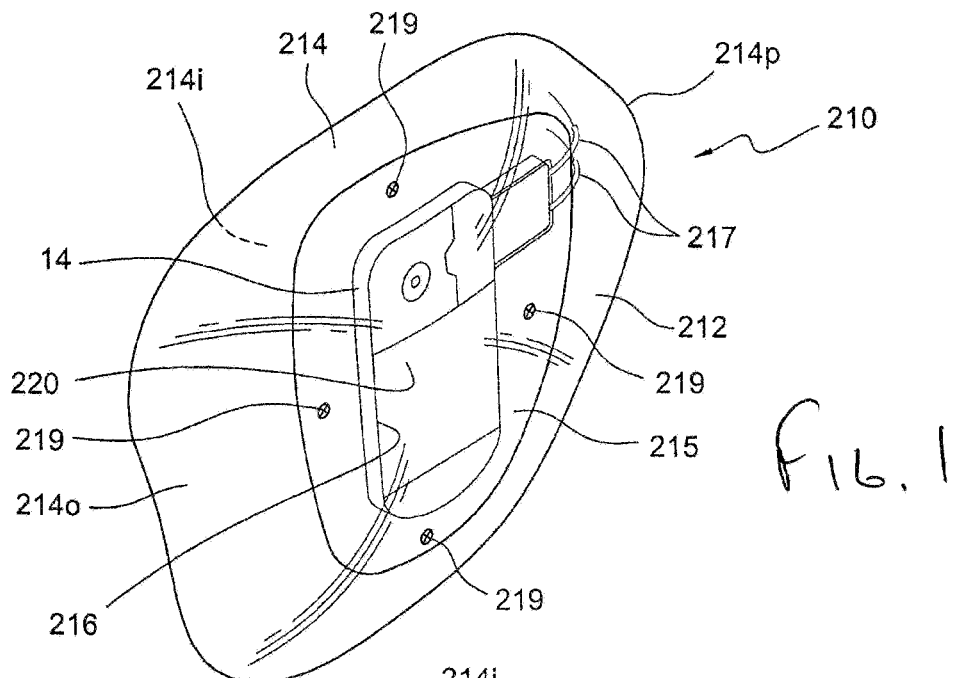
FIG. 1 is a perspective view of a low-profile intercranial device in accordance with the present invention.
Figure 2:
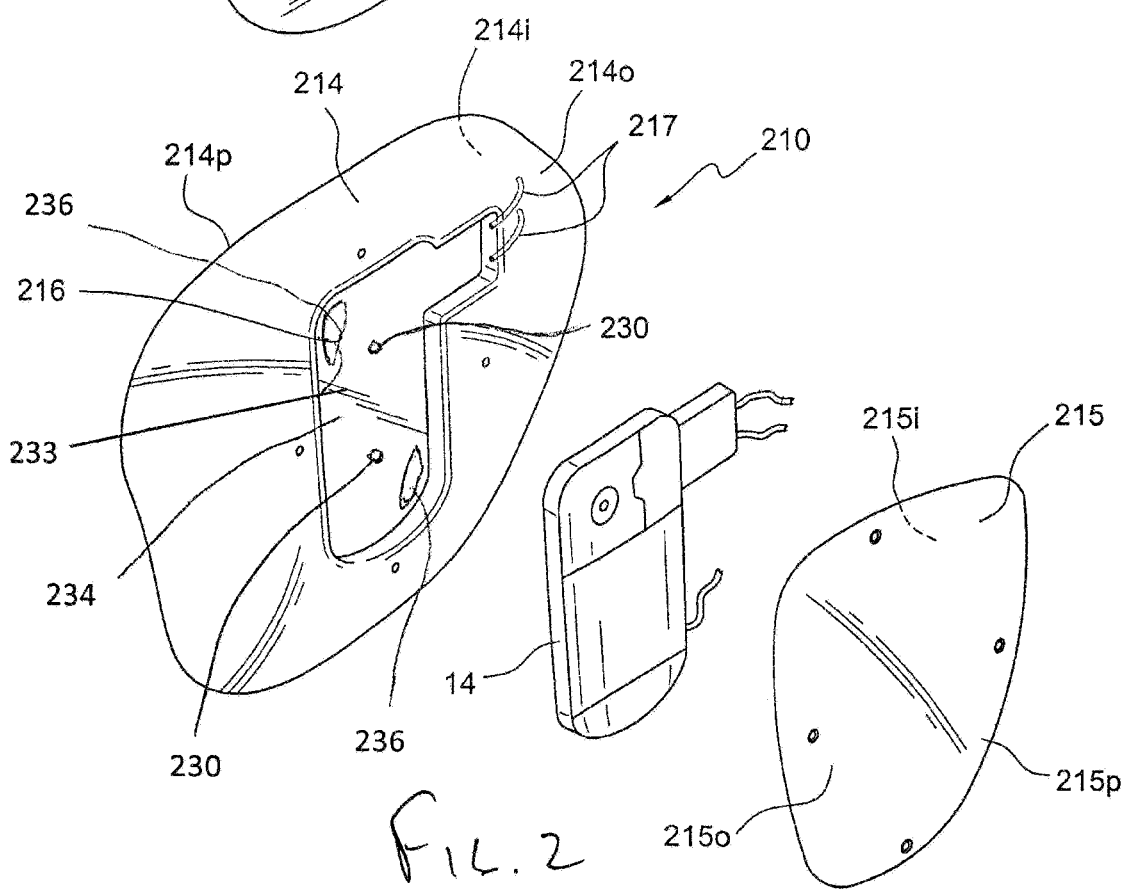
FIG. 2 is an exploded view of the low-profile intercranial device shown in FIG. 1.

The detailed embodiments are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention. For example, while the disclosure is preferably directed to a low-profile intercranial device that includes a customized cranial implant, it is within the scope of the disclosure that the cranial implant could be fabricated and provided as a standardized shape or size implant configured to receive a standard size and shape functional implant, rather than a patient-specific customized implant designed to conform to the skull opening. This is especially the case where skull resection is not determined, for example, by the shape of a resected tumor and may be created in a standardized manner specifically to accommodate the low-profile intercranial device of the present disclosure.

As used within this disclosure, the term "intercranial" means situated or occurring within the cranium itself such that such devices are positioned within the space existing between the inner surface of the scalp and the outer surface of the dura. As such, intercranial devices are those devices intended for positioning within the cranium itself as opposed to devices that may be positioned on or adjacent to the cranium or positioned along the interior of the cranium, for example, between the cerebral cortex and the interior surface of the cranium. With this in mind, intercranial devices such as those discussed below replace resected portions of the cranium due to abnormalities in the cranium, damage to the cranium, or other medically sufficient reasons for resecting positions of the cranium.

With reference to the various figures, a low-profile intercranial device 210 composed of a static cranial implant 212 and a functional neurosurgical implant 14 is disclosed. As those skilled in the art will appreciate, many functional neurosurgical implants (as described below) 14 require grounding to operate properly (for example, taking accurate impedance measurements) and, as will be explained below in greater detail, the structure of static cranial implant 212 facilitates contact of the functional neurosurgical implant 14 with bodily fluid which acts to conveniently and reliably ground the neurosurgical implant 14.

The static cranial implant 212 in accordance with this embodiment includes a base cranial implant member 214 and a cover cranial implant member 215. The base cranial implant member 214 has a geometry that substantially conforms with a resected portion of the patient's anatomy to which the low-profile intercranial device 210 is to be secured. The base cranial implant member 214 includes an outer (commonly convex) first surface 214o, an inner (commonly concave) second surface 214i, and a peripheral edge 214p extending between the outer first surface 214o and the inner second surface 214i. The customized static cranial implant 212 is shaped and dimensioned for engagement with the skull of the patient upon implantation in a manner well known to those skilled in the field of neurosurgical procedures. The outer first surface 214o and inner second surface 214i of the base cranial implant member 214 are preferably curved in a superior to inferior direction, a posterior to anterior direction, and a medial to lateral direction.

The base cranial implant member 214 also includes a center recess 216 formed along the outer first surface 214o and optional structural elements 217, for example, channels, pockets, access holes, and/or other structural elements, designed to accommodate various features of the functional neurosurgical implant 14. As with the prior embodiment, multiple recesses may be employed where the functional neurosurgical implant(s) being used dictates and that the recess need not be directly in the center of the base cranial implant member but may be offset as dictated by the procedure being performed.

The center recess 216 is defined by internal side walls 216sw and a recess base surface 233. The portion of the body of the cranial implant member 214 positioned between the inner second surface 214i and the recess base surface 233 is considered to define the recess base body 234. The base body 234 is provided with a plurality of fluid passageways 236 extending between the inner second surface 214i and the recess base surface 233 so as to allow for the flow of bodily fluid between the external environment of the cranial implant member 214 and the cavity 220 defined by the center recess 216 and the cover cranial implant member 215. With the free flow of bodily fluid between the external environment of the cranial implant member 214 and the cavity 220 defined by the center recess 216 and the cover cranial implant member 215 the functional neurosurgical implant 14 is conveniently and reliably grounded to ensure proper impedance measurements.

In accordance with a disclosed embodiment, the fluid passageways 236 are crescent shaped apertures formed in the recess base body 234. While crescent shaped apertures are disclosed in accordance with the present embodiment, the fluid passageways 236 may take a variety of shapes without departing from the spirit of the present invention. Further, while the disclosed embodiment provides a plurality of fluid passageways, it is appreciated at least one or more fluid passageways may be used in accordance with the present invention.

In accordance with a preferred embodiment, the fluid passageways 236 are formed in opposed corners of the center recess 216. While the specific location of the fluid passageways 236 is not critical to operation of the neurosurgical implant 14, care should be taken to place the fluid passageways 236 in a position wherein positioning of the neurosurgical implant 14 relative to the resected portion of the cranium, the dura, and the brain is optimized. For example, it is important to position the fluid passageways 236 in such a way that bodily fluid flow is unimpeded between the external environment of the cranial implant member 214 and the cavity 220 defined by the center recess 216. With this in mind, the use of multiple fluid passageways 236 minimizes the possibility of pressure differentials that might inhibit the flow of bodily fluid between the external environment and the cavity 220. Further still, care should be taken to ensure that the neurosurgical implant 14 does not cover a fluid passageway(s) 236 in a manner that might prevent the desired flow of bodily fluid between the external environment and the cavity 220. With this in mind, the disclosed embodiment positions the fluid passageways 236 at the first and second ends of the center recess 216.

While oppositely positioned fluid passageways 236 may be optimal for some circumstances, the shape and positioning of the fluid passageways 236 will ultimately be decided on a case by case basis. The location of the fluid passageways 236 will be determined when the position of the cranial implant member 214 relative to the cranium and the position of the functional neurosurgical implant 14 within the cranial implant member 214 are determined and approved. Once these factors are determined, the furthest penetration point (s) of the low-profile intercranial device 210 into the cranium is identified. By positioning the fluid passageway(s) 236 at that position, that is, the point(s) at which the low-profile intercranial device 210 penetrates the furthest into the cranium, it is possible to lessen that penetration anywhere from approximately 1 mm to approximately 3 mm by forming the fluid passageway(s) 236 apertures at this location(s).

Positioning of the cranial implant member 214 relative to the dura is also enhanced by the provision of suture holes within the recess base surface 233 of the cranial implant member 214. The surgical holes 230 allow a surgeon to pass sutures 232 through the suture holes 230 and use the suture 232 to draw the dura into a close relationship with the cranial implant member 214. By drawing the dura into close relationship with the cranial implant member 214, in particular, the inner second surface 214i of the cranial implant member 214, the space therebetween is minimized and potential for pooling of cerebrospinal fluid is minimized which thereby minimizes the potential for infections. Considering the positioning of the suture holes 230, it is appreciated there may be instances where a channel runs the entire length of the recess opposite openings for leads. In such a situation, suture holes are placed no more than 10 mm away from the fluid passageway(s). It is appreciated that the fluid passageway could double as a suture hole and are used in conjunction to the suture holes.

In addition to functioning as a ground ensuring proper measurement of impedance by the functional neurosurgical implant of the low-profile intercranial device by allowing the cavity to pool with cerebrospinal fluid, the fluid passageway(s) also allow for the low-profile intercranial device to equalize internal pressure. The free flow of bodily fluid through the fluid passageway(s) can also help regulate the temperature of the functional neurosurgical implant if it generates excess heat while functioning, serve as a thermal energy source for the functional neurosurgical implant if the implant utilizes thermal energy harvesting as its power source, provide energy to the functional neurosurgical implant through motion harvesting (for example, consider water flowing over a water wheel) or through biofuels (for example, harvesting energy from glucose, etc.). As a result, the fluid passageways are shaped and dimensioned to allow for fluid communication syphoning heat from the intercranial device, allow for fluid communication syphoning cold from the intercranial device, and/or prevent fluid accumulation within the intercranial device.

In accordance with a preferred embodiment, the base cranial implant member 214 is fabricated from a wide array of commonly-available biomaterials including, but not limited to, clear and/or opaque PMMA (Poly(methyl methacrylate)), PEEK (Polyether ether ketone), PEKK (Polyetherketoneketone), porous polyethylene, titanium alloy, and/or various other tissue-engineered constructs. In accordance with one embodiment, the base cranial implant member 214 is ideally made of a clear PMMA since it's completely transparent and fully lucent. This allows for novel inspection of the interdigitated functional neurosurgical implant 14 and neighboring components.

In addition to the base cranial implant member 214, and as briefly discussed above the customized static cranial implant 212 includes a cover cranial implant member 215. The cover cranial implant member 215 is shaped and dimensioned for positioning over the center recess 216 along the outer first surface 214o of the base cranial implant member 214. In accordance with a preferred embodiment, the cover cranial implant member 215 is secured to the base cranial implant member 214 by screw fixation 219. The cover cranial implant member 215 includes an outer (commonly convex) first surface 215o, an inner (commonly concave) second surface 215i, and a peripheral edge 215p shaped and dimensioned for engagement with the outer first surface 214o of the base cranial implant member 214 along the periphery of the center recess 216. As with the base cranial implant member 214, the outer first surface 215o and inner second surface 215i of the cover cranial implant member 215 are preferably curved in a superior to inferior direction, a posterior to anterior direction, and a medial to lateral direction.

The base cranial implant member 214 and the cover cranial implant member 215 have a total thickness appropriate for positioning within the intercranial space. Depending on the strength characteristics of the materials used, the base cranial implant member 214 and the cover cranial implant member 215 will have a thickness (with areas of strategic bulking and/or thinning) of around 1 millimeter to 25 millimeters, preferably, 1 millimeter to 12 millimeters.

As mentioned above, the cover cranial implant member 215 fits over the center recess 216 along the outer first surface 214o of the base cranial implant member 214. In this way, the inner second surface 215i of the cover cranial implant member 215 and the outer first surface 214o of the base cranial implant member 214, along the center recess 216, define a center cavity 220 configured to conform to the exact requirements of the functional neurosurgical implant 14 in accordance with the present invention. With this in mind, the inner second surface 215i of the cover cranial implant member 215 may be shaped and/or contoured to enhance the positioning of the functional neurosurgical implant 14 within the center cavity 220. As discussed above, it is this center cavity 220 that is maintained in fluid communication with the external environment through the application of holes discussed above.

The functional neurosurgical implant 14 of the present invention is selected from a variety of FDA-approved and experimental options for electrical, optical, mechanical, medicinal and other treatment/monitoring devices designed for long term invasive treatment and/or disease-monitoring of patients requiring such attention. These functional neurosurgical implants 14 are known devices manufactured by various vendors within the neurosurgical industry and have known, unmodifiable dimensions that may be used in the modification of the customized static cranial implant 212 to optimize surgical results by minimizing abnormal shapes, visible contours, and/or craniofacial deformities.

Based upon the functional neurosurgical implant 14 used in conjunction with the present invention, the functional neurosurgical implant 14 may be useful in the treatment of various patient conditions such as epilepsy, movement disorders, chronic pain, spasticity, cerebral palsy, multiple sclerosis, spinal cord injury, traumatic brain injury, attention-deficit/hyperactivity disorder, autism, etc.—and the potential to obtain supra-normal levels of brain function in both military and civilian situations. Furthermore, incorporation of imaging devices within cranial implants could help to provide ongoing tumor bed monitoring for early detection of disease recurrence.

By way of example, one potential functional neurosurgical implant 14 that may be employed in accordance with the present invention is a battery-powered functional neurosurgical implant known as the NeuroPace® device, that is, a device for responsive neurostimulation for epilepsy, which has a design flaw in that it limits the visible aesthetic result due to its irregular shape(s), requires placement of battery (ies) within extra anatomical locations, and suffers from high rates of implant micromotion thereby leading to common device infection and bone flap osteomyelitis (See, Wei Z, Gordon C R, Bergey G K, Sacks J M, Anderson W S. Implant Site Infection and Bone Flap Osteomyelitis Associated with the NeuroPace Responsive Neurostimulation System. World Neurosurg 2015 Dec. 29; pii: s1878-8750 (15)01775-1.) These deficiencies are overcome in accordance with the present invention by optimizing the customized static cranial implant 212 for receipt of the NeuroPace® device.

Further, the present invention allows the possibility of combining the benefits of the ideal contour customized static cranial implant 212 with the efficacy of neuromodulation potentially reducing the complication rates of repetitive nerve stimulation (RNS) to the complication rates of cranial reconstruction (50% to 3-4%) and giving surgeons an option when the existing bone is resorbing.

With the foregoing in mind, additional functional neurosurgical implants 14 that may be used in conjunction with the present invention include, but are not limited to the following: Deep Brain Stimulators (DBS); Cortical Brain Stimulators (CBS); neurologic medicines that are otherwise prevented from diffusing through the blood-brain barrier via common delivery methods; battery/passively/kinetically/or otherwise-powered functional devices including neuromodulation devices, imaging devices, radiation therapy devices, and remote sensing/monitoring devices; monitoring devices for abnormal levels of intracranial pressure (ICP) or brain activity (i.e., seizures), such as an electrical array for motor/vision cortex control, battery/passively/kinetically/or otherwise-based stimulation hardware for epilepsy management (grids/batteries/wires); low-profile remote imaging devices (e.g., optical coherence tomography (OCT), duplex ultrasound); delivery/sensing devices for electrical impulses; neurological and physiological systems required for deep space/sleep functionalities enhancing the monitoring and/or maintenance of bodily vital signs, nutrition, cognition, etc.; convection enhanced delivery systems effectively delivering therapeutics to substantial volumes of brain and brain tumor; and remote neuro-imaging devices (i.e., electroencephalogram (EEG).

With this in mind, the term "functional neurosurgical implant" is meant to reference any therapeutic hardware or compositions including, but not limited to, medicines to treat any patient-specific illness, or electronic, mechanical, imaging modality and/or electro-mechanical device to remotely monitor (e.g., via Wi-Fi connectivity) or intervene any specific neurologic illness, including imaging, monitoring, electrostimulation, radiation therapy, polarized light/laser neuronal modulation devices. The term "functional" denotes the fact that these implants provide the low-profile intercranial device 10 with the ability to function as more than a safe custom-shaped skull replacement by providing various functionalities, for example, local drug delivery, monitoring (such as brain monitoring), or local electric stimulation to the patient.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A low-profile intercranial device adapted for housing a functional neurosurgical implant in manner providing for convenient and reliable grounding to ensure proper impedance measurements, comprising:
   a static cranial implant including a base cranial implant member including an outer first surface, an inner second surface, and a recess shaped and dimensioned for receiving a functional neurosurgical implant;
   at least one fluid passageway providing for convenient and reliable grounding of a functional neurosurgical implant, the at least one fluid passageway extending between the inner second surface and the recess allowing for the flow of bodily fluid between an external environment of the base cranial implant member and a cavity defined by the recess to thereby conveniently and reliably ground the functional neurosurgical implant to ensure proper impedance measurements of the functional neurosurgical implant;
   wherein the at least one fluid passageway is a crescent shaped aperture.

2. The intercranial device according to claim 1, wherein the static cranial implant further includes a cover cranial implant member.

3. The intercranial device according to claim 1, wherein the base cranial implant member has a geometry that substantially conforms with a resected portion of the patient's anatomy.

4. The intercranial device according to claim 1, wherein the recess includes internal side walls and a recess base surface, and the at least one fluid passageway extends between the inner second surface and the recess base surface.

5. The intercranial device according to claim 1, further including a functional neurosurgical implant positioned within the recess.

6. The intercranial device according to claim 1, wherein the at least one fluid passageway includes a plurality of fluid passageways.

7. The intercranial device according to claim 6, wherein the plurality of fluid passageways are formed in opposed corners of the recess.

8. The intercranial device according to claim 1, further including suture holes within a recess base surface of the recess.

9. The intercranial device according to claim 1, wherein the base cranial implant member is made of a clear material.

10. A low-profile intercranial device adapted for housing a functional neurosurgical implant in manner providing for convenient and reliable grounding to ensure proper impedance measurements, comprising:
    a static cranial implant including a base cranial implant member including an outer first surface, an inner second surface, and a recess shaped and dimensioned for receiving a functional neurosurgical implant;
    at least one fluid passageway providing for convenient and reliable grounding of a functional neurosurgical implant, the at least one fluid passageway extending between the inner second surface and the recess allowing for the flow of bodily fluid between an external environment of the base cranial implant member and a cavity defined by the recess to thereby conveniently and reliably ground the functional neurosurgical implant to ensure proper impedance measurements of the functional neurosurgical implant;
    wherein the at least one fluid passageway is shaped and dimensioned to allow for fluid communication syphoning heat from the intercranial device.

11. The intercranial device according to claim 10, wherein the static cranial implant further includes a cover cranial implant member.

12. The intercranial device according to claim 10, wherein the base cranial implant member has a geometry that substantially conforms with a resected portion of the patient's anatomy.

13. The intercranial device according to claim 10, wherein the recess includes internal side walls and a recess base surface, and the at least one fluid passageway extends between the inner second surface and the recess base surface.

14. The intercranial device according to claim 10, further including a functional neurosurgical implant positioned within the recess.

15. The intercranial device according to claim 10, wherein the at least one fluid passageway includes a plurality of fluid passageways.

16. The intercranial device according to claim 15, wherein the plurality of fluid passageways are formed in opposed corners of the recess.

17. The intercranial device according to claim 10, further including suture holes within a recess base surface of the recess.

18. The intercranial device according to claim 10, wherein the base cranial implant member is made of a clear material.

19. A low-profile intercranial device adapted for housing a functional neurosurgical implant in manner providing for convenient and reliable grounding to ensure proper impedance measurements, comprising:
    a static cranial implant including a base cranial implant member including an outer first surface, an inner second surface, and a recess shaped and dimensioned for receiving a functional neurosurgical implant;

at least one fluid passageway providing for convenient and reliable grounding of a functional neurosurgical implant, the at least one fluid passageway extending between the inner second surface and the recess allowing for the flow of bodily fluid between an external environment of the base cranial implant member and a cavity defined by the recess to thereby conveniently and reliably ground the functional neurosurgical implant to ensure proper impedance measurements of the functional neurosurgical implant;

wherein the at least one fluid passageway is shaped and dimensioned to allow for fluid communication syphoning cold from the intercranial device.

20. The intercranial device according to claim 19, wherein the static cranial implant further includes a cover cranial implant member.

21. The intercranial device according to claim 19, wherein the base cranial implant member has a geometry that substantially conforms with a resected portion of the patient's anatomy.

22. The intercranial device according to claim 19, wherein the recess includes internal side walls and a recess base surface, and the at least one fluid passageway extends between the inner second surface and the recess base surface.

23. The intercranial device according to claim 19, further including a functional neurosurgical implant positioned within the recess.

24. The intercranial device according to claim 19, wherein the at least one fluid passageway includes a plurality of fluid passageways.

25. The intercranial device according to claim 24, wherein the plurality of fluid passageways are formed in opposed corners of the recess.

26. The intercranial device according to claim 19, further including suture holes within a recess base surface of the recess.

27. The intercranial device according to claim 19, wherein the base cranial implant member is made of a clear material.

28. A low-profile intercranial device adapted for housing a functional neurosurgical implant in manner providing for convenient and reliable grounding to ensure proper impedance measurements, comprising:

a static cranial implant including a base cranial implant member including an outer first surface, an inner second surface, and a recess shaped and dimensioned for receiving a functional neurosurgical implant;

at least one fluid passageway providing for convenient and reliable grounding of a functional neurosurgical implant, the at least one fluid passageway extending between the inner second surface and the recess allowing for the flow of bodily fluid between an external environment of the base cranial implant member and a cavity defined by the recess to thereby conveniently and reliably ground the functional neurosurgical implant to ensure proper impedance measurements of the functional neurosurgical implant;

wherein the at least one fluid passageway is shaped and dimensioned to prevent fluid accumulation within the intercranial device.

29. The intercranial device according to claim 28, wherein the static cranial implant further includes a cover cranial implant member.

30. The intercranial device according to claim 28, wherein the base cranial implant member has a geometry that substantially conforms with a resected portion of the patient's anatomy.

31. The intercranial device according to claim 28, wherein the recess includes internal side walls and a recess base surface, and the at least one fluid passageway extends between the inner second surface and the recess base surface.

32. The intercranial device according to claim 28, further including a functional neurosurgical implant positioned within the recess.

33. The intercranial device according to claim 28, wherein the at least one fluid passageway includes a plurality of fluid passageways.

34. The intercranial device according to claim 33, wherein the plurality of fluid passageways are formed in opposed corners of the recess.

35. The intercranial device according to claim 28, further including suture holes within a recess base surface of the recess.

36. The intercranial device according to claim 28, wherein the base cranial implant member is made of a clear material.

* * * * *